United States Patent [19]

Hirano et al.

[11] Patent Number: 5,252,673
[45] Date of Patent: Oct. 12, 1993

[54] MACROMOLECULAR MITOMYCIN C DERIVATIVE AND METHOD FOR PRODUCTION THEREOF

[75] Inventors: Takashi Hirano; Takeshi Todoroki; Shinichi Ohashi, all of Tsukuba, Japan

[73] Assignees: Agency of Industrial Science & Technology; Ministry of International Trade & Industry, Tokyo, Japan

[21] Appl. No.: 850,988

[22] Filed: Mar. 12, 1992

[30] Foreign Application Priority Data

Mar. 18, 1991 [JP] Japan ................................ 3-77195

[51] Int. Cl.$^5$ ............................................ C08L 77/00
[52] U.S. Cl. ................................ 525/183; 525/178; 525/937
[58] Field of Search .......................................... 525/183

[56] References Cited

U.S. PATENT DOCUMENTS 4,520,162  5/1985  Hirano et al. ................... 525/327.6

OTHER PUBLICATIONS

Cancer Research vol. 34, Mar. 1974 pp. 506–511 Page S. Morahan, et al: Antitumor Action of Pyran Copolymer and Tilorone Against Lewis Lung Carcinoma and B–16 Melanoma.

Cancer Treatment Reports vol. 62, No. 11, Nov. 1978 pp. 1791–1796, Robert L. Stolfi, et al: Therapeutic Activity of Maleic Anhydride-Vinyl Ether Copolymers Against Spontaneous, Autochthonous Muring Mammary Tumors.

Cancer Research 41, Oct. 1981, pp. 3901–3907. Scott E. Loveless, et al: Maleic Vinyl Ether Murine Macrophages Against Lung-Metastasizing Tumors.

*Primary Examiner*—Ana L. Carrillo
*Attorney, Agent, or Firm*—Oblon, Spivak, McClelland, Maier & Neustadt

[57] ABSTRACT

A macromolecular mitomycin derivative excellent in antitumor ability is produced by causing a specific divinyl ether-maleic anhydride copolymer to react with a specific aminocarboxylic acid and causing mitomycin C to react on the resultant reaction product. The derivative is optionally converted into a pharmacologically acceptable salt.

4 Claims, 3 Drawing Sheets

MACROMOLECULAR MITOMYCIN C DERIVATIVE AND METHOD FOR PRODUCTION THEREOF

BACKGROUND OF THE INVENTION

1. Field of the Invention

This invention relates to a novel macromolecular mitomycin C derivative having low toxicity and excelling in the antitumor activity, and methods for the production of the derivative and the salt.

2. Prior Art Statement

In recent years, numerous known antibiotics have been demonstrated as possessing an outstanding antitumor activity. Among the antitumor antibiotics introduced to the art, mitomycin C is a representative antitumor agent produced in Japan. It produces an outstanding curative effect on sarcoma, leukemia, deciduocellular sarcoma, epithelioma, and cancer of the bladder and has been finding extensive utility in clinical applications.

While the mitomycin C possesses a remarkable antitumor effect, however, it exhibits strong toxicity to normal cells and induces discernible side effects such as decreases in leukocytes and thrombocytes, accelerated hemorrhage, and hepatic disorders. In the administration of mitomycin C, these side effects should be carefully considered so as not to induce them.

When the antitumor active substance of such a low molecular compound as mitomycin C is conjugated to a macromolecular compound, this antitumor active substance is gradually released from the macromolecular compound in the patient's body, retains its concentration in the blood, is allowed to vary the body distribution and, therefore, is expected to inhibit the side effects and increase the antitumor activity.

As respects the mitomycin C, the combination thereof with dextran, a plasma extender, has been known as what will answer the expectation just mentioned (Japanese Patent Public Disclosure SHO 54(1979)-97691. Since dextran, a natural produce, is difficult of chemical modification, the ratio of fixed mitomycin C in the conjugate is only about 10% at most.

In the circumstances, there has existed an earnest desire for a macromolecular compound capable of combining mitomycin C therewith in a high ratio.

SUMMARY OF THE INVENTION

The inventors, in view of the true state of affairs described above, have continued a diligent study on macromolecular compounds for combination with the mitomycin C, to find that a divinyl ether-maleic anhydride copolymer serves as an effective macromolecular carrier. This invention has been perfected as a result.

To be specific, this invention is directed to a macromolecular mitomycin derivative having repeating units represented by the formula:

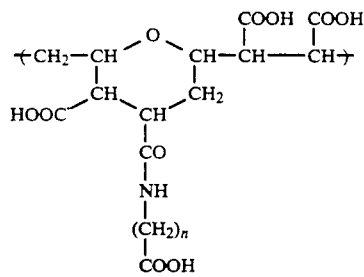

wherein n stands for an integer in the range of from 1 to 11 and repeating units represented by the formula:

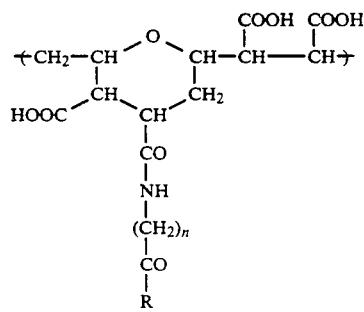

wherein R stands for a mitomycin C residue represented by the formula:

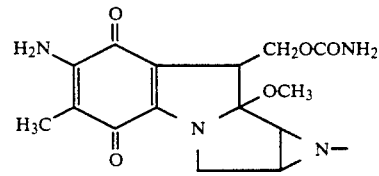

and n for an integer in the range of from 1 to 11, the total number of the repeating units of the two species mentioned above is not less than 10 and not more than 500, and the molar ratio of the repeating units represented by the formula (1) to the repeating units represented by the formula (2) is in the range of from 0:100 to 90:10, to a salt of the mitomycin derivative and to methods for the production of the macromolecular mitomycin derivative and the salt thereof, which methods comprise causing a divinyl ether-maleic anhydride copolymer represented by the formula:

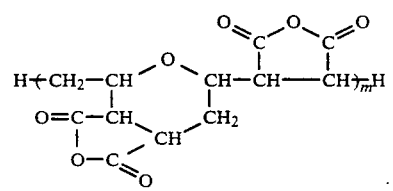

wherein m stands for an integer of not less than 10 and not more than 500 to react with an aminocarboxylic acid represented by the formula:

$$H_2N(CH_2)_nCOOH \quad (4)$$

wherein n stands for an integer of not less than 1 and not more than 11 in the presence of an organic solvent and then causing mitomycin C to react upon the product of the reaction.

The above and other features of the invention will become apparent from the following description made with reference to the accompanying drawings.

DESCRIPTION OF THE PREFERRED EMBODIMENTS

Figure 1:
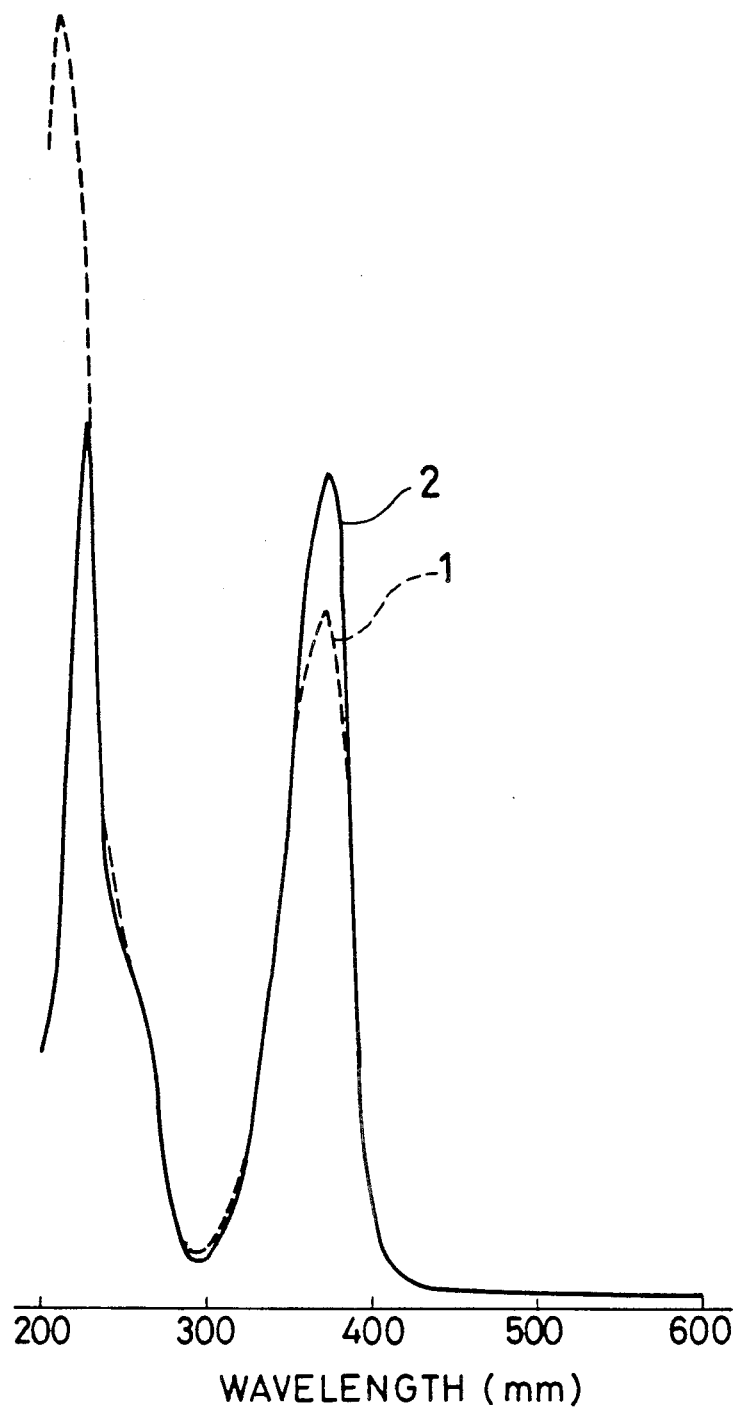
FIG. 1 is an ultraviolet absorption spectrum of mitomycin C taken in distilled water for the purpose of comparison with a macromolecular mitomycin C derivative in any of Examples.

First, the divinyl ether-maleic anhydride copolymer itself possesses an excellent antitumor activity (Cancer Research 41, 3901–3906, October 1981) and, in combination with an antitumor agent, manifests a synergistic antitumor activity. Then, since the divinyl ether-maleic anhydride copolymer possesses many acid anhydride groups with high reactivity, it readily reacts with various amino acids, allows insertion therein of spacers at a high rate, and allows the content of mitomycin C units conjugated to the ends of such spacers to be four times the level obtained by the conventional inventions.

As the mitomycin C possesses a hydrophobic structural moiety, the macromolecular mitomycin C conjugate with a high content of mitomycin C is in general assumed to be insoluble in water. But the conjugate of mitomycin C with the divinyl ether-maleic anhydride copolymer exhibits high water solubility, because it possesses numerous carboxyl groups and contains hydrophilic pyrane rings in the main chain thereof. The mitomycin C conjugated to the divinyl ether-maleic anhydride copolymer is gradually released in human plasma under mild conditions.

Thus, the divinyl ether-maleic anhydride copolymer serves as an excellent carrier for the mitomycin C.

The divinyl ether-maleic anhydride copolymer represented by the aforementioned formula (3) which is used in this invention is obtained by copolymerizing divinyl ether with maleic anhydride by the known method.

This divinyl ether-maleic anhydride copolymer in itself manifests an outstanding antitumor effect on various solid tumors. This copolymer of a molecular weight of not more than 100,000 possesses low toxicity and proves suitable as a carrier for the mitomycin C.

The mitomycin C which is used as an antitumor active substance in this invention produces an excellent antitumor effect on sarcoma, leukemia, Hodgkin's disease, malignant deciduocellular sarcoma, epithelioma, and cancer of the bladder.

The macromolecular mitomycin C derivative of this invention is obtained by dissolving the aforementioned divinyl ether-maleic anhydride copolymer in such an organic solvent as N-methyl pyrrolidone, causing the resultant solution to react with a varying aminocarboxylic acid, then subjecting the product of this reaction to a conjugation reaction with mitomycin C, cleaning the product of this linking reaction with an ultrafiltration membrane thereby removing substances other than the product aimed at, and freeze drying the residue of the filtration. The product of the conjugation reaction, when desired, may be converted into a pharmacologically allowable salt such as a sodium salt, potassium salt, calcium salt, or magnesium salt, subjected to ultrafiltration, freeze dried, and taken out as a salt. Generally, a macromolecular substance inevitably has a molecular weight distribution. By repeating the ultrafiltration in this method, there can be obtained a macromolecular mitomycin C derivative which has a relatively small molecular weight distribution. In the macromolecular mitomycin C derivative obtained as described above, the content of mitomycin C is desired to be in the range of from 5 to 45% by weight. The limit, 45% by weight, corresponds to the case in which the proportion of the units represented by the formula (1) mentioned above is 0 and the derivative has a high content of mitomycin C linked one each to the repeating units.

If the total number of the repeating units represented by the formulas (1) and (2) is less than 10, the product fails to manifest the effect aimed at by this invention. When this total number exceeds 500, the toxicity of the product increases to an unduly high level. Therefore, the total number of the repeating units is preferably in the range of from 100 to 300.

The organic solvents which can be used in this invention from the practical point of view include anhydrous N-methylpyrrolidone, dimethyl sulfoxide, and acetone, for example.

The macromolecular mitomycin C derivative and the salts thereof according to this invention gradually release mitomycin C, an antitumor active substance, under the same mild conditions as those in vivo. The compound which satisfies the formulas (1) and (2) on the condition of $n=5$, for example, releases 50% of the mitomycin C linked thereto within the span of 2.7 days in human plasma kept in a test tube at 37° C. The speed of this release can be adjusted by the length of the spacer. The number of days required for the release of 50% of the combined mitomycin C is 1.8 days in the compound having the condition of $n=1$ and 12.0 days in the compound having the condition of $n=11$. The speed of the release does not depend on the molecular weight of the divinyl ethermaleic anhydride copolymer. The length of the spacer forms the main cause for controlling the speed of the release.

As respects the antitumor activity of the macromolecular mitomycin C derivative of this invention, B16 mouse melanotic melanoma was used for evaluation. Viable $5\times10^5$ B16 cells were inoculated subcutaneously in BD2F$_1$ mice and drug was intraveneously administered 12 days after the tumor inoculation. The macromolecular mitomycin C derivative could inhibit 87.7% tumor growth in comparison with the control mice. Mitomycin C alone could inhibit only 66.7%.

As described above, the macromolecular mitomycin C derivative of this invention enjoys an outstanding ability to effect controlled release of mitomycin C and manifests low toxicity and, owing to the synergistic effect produced in conjunction with the divinyl ether-maleic anhydride copolymer which is itself possesses an antitumor activity, exhibits a highly satisfactory antitumor effect as compared with the mitomycin C used alone.

Now, this invention will be described more specifically below with reference to working examples. The term "divinyl ether-maleic anhydride copolymer" will be referred to briefly as "DIVEMA" hereinafter.

EXAMPLE 1

A solution of 800 mg of DIVEMA (average molecular weight 30,000) in 5 ml of anhydrous N-methyl pyrrolidone was added to a solution of 3.2 g of 6-aminohexanoic acid in 5 ml of distilled water with magnetic stirring. During this addition, the pH of the solution was adjusted to 9.0 with an aqueous 2M sodium hydroxide solution. After completion of the reaction, the solution was stirred at a pH 9.0 for two hours. The resultant reaction solution was diluted with 500 ml of distilled water, then the pH was adjusted to 4.0 with 6M hydrochloric acid. The thus obtained solution was passed through a PTHK membrane (fractionation molecular weight 100,000) produced by Millipore Corp. and the resultant filtrate was filtered by a PM30 membrane (fractionation molecular weight 30,000) produced by Amicon Corp. The residue was lyophilized to obtain 900 g of a freeze dry product. The freeze dry product was found to be DIVEMA containing 6-aminohexanoic acid as a spacer. In a solution of 36 mg of the DIVEMA-6-aminohexanoic acid in 4 ml of distilled water, 52 mg of water-soluble carbodiimide was added to react for 30 minutes. The resultant reaction mixture and a solution of 50 mg of mitomycin C in 20 ml of water were stirred in a shaded place at room temperature for 24 hours.

The resultant reaction mixture was subjected to ultrafiltration over a PCAC membrane (fractionation molecular weight 1,000) produced by Millipore Corp. against distilled water to remove the unreacted mitomycin C. The ultrafiltration was continued until the absorbance, $OD_{364\ nm}^{10\ mm}$ of the filtrate fell below 0.01. The filtrate was subjected to sterilizing filtration with a Millipore filter having a pore diameter of 0.1 $\mu$m. The filtrate from this filtration was freeze dried. The product, 73 mg in weight, was a purple cotton-like solid which was easily soluble in water and physiological saline. As illustrated in FIG. 1, the ultraviolet spectrum of this product in distilled water showed an absorption peak 1 peculiar to mitomycin C at 364 nm. From the calibration curve, the mitomycin C content of this product was calculated to be 39.6% by weight. The absorption peak 2 denotes the ultraviolet absorption spectrum of mitomycin C in distilled water.

EXAMPLE 2

The aqueous solution of the macromolecular mitomycin C derivative obtained in Example 1 was adjusted to pH 7.6 with an aqueous 0.1 M sodium hydrogen carbonate solution, cleaned by ultrafiltration with a PCAC membrane produced by Millipore Corp. against distilled water, then subjected to sterilizing filtration with a Millipore filter having a pore diameter of 0.1 $\mu$m, and freeze dried. This procedure produced a purple cotton-like solid quantitatively. This product showed higher solubility in water and physiological saline than the product obtained in Example 1. The ultraviolet absorption spectrum of this product was identical with that of the product of Example 1.

EXAMPLE 3

In the same manner as in Example 1, a solution of 1.0 g of DIVEMA (average molecular weight 30,000) in 5 ml of N-methyl pyrrolidone was added to a solution of 1.3 g of 3-aminopropionic acid in 5 ml of distilled water with magnetic stirring. During this addition, the pH of the solution was kept at 9.0 with an aqueous 2M sodium hydroxide solution. After the reaction, the resultant mixed solution was stirred at pH 9.0 for two hours. The produced reaction solution was diluted with 500 ml of distilled water, adjusted to pH 4.0 with 6M hydrochloric acid. The solution thus obtained was passed through a YM100 membrane (fractional molecular weight 100,000) produced by Amicon Corp. and the resultant filtrate was filtered by a PM30 membrane (fractionation molecular weight 30,000) produced by the same corporation. The residue was lyophilized to obtain 550 mg of a freeze dried product. This product was found to be DIVEMA containing 3-aminopropionic acid as a spacer. By causing 32 mg of the DIVEMA-3-aminopropionic acid to react with 50 mg of mitomycin C in the same manner as in Example 1 and treating the reaction product in the same manner as in Example 1, there was obtained 64 mg of a purple cotton-like solid. From the absorption of the ultraviolet spectrum at 364 nm, this product was found to contain 43.5% by weight of mitomycin C. The ultraviolet absorption spectrum of this product was identical with that of the product of Example 1.

EXAMPLE 4

In the same manner as in Example 1, a solution of 350 mg of DIVEMA (average molecular weight 30,000) in 2 ml of N-methyl pyrrolidone was added to a solution prepared by suspending 1.0 g of 12-aminododecanoic acid in 25 ml of distilled water and then homogenizing the resultant suspension in an aqueous 6M sodium hydroxide solution, with the latter solution kept stirred. The resultant mixed solution was stirred at room temperature for two hours, diluted with 500 ml of distilled water, adjusted to pH 7.0 with 6M hydrochloric acid, and purified by a PM30 membrane (fractional molecular weight 30,000) produced by Amicon Corp. against distilled water. The resultant solution was adjusted to pH 5.0 with 2M hydrochloric acid and passed through a PTHK membrane (fractional molecular weight 100,000) produced by Millipore Corp. The resultant filtrate was filtered by a PM30 membrane produced by Amicon Corp. The residue was lyophilized to obtain 400 mg of a freeze dried product. This product w as found to be DIVEMA having 12-aminododecanoic acid as a spacer. By causing 44 mg of the DIVEMA-12-aminohexanoic acid to react with 50 mg of mitomycin C in the same manner as in Example 1 and treating the reaction product in the same manner as in Example 1, there was obtained 86 mg of a purple cotton-like solid. From the absorption of the ultraviolet spectrum at 364 nm, this product was found to contain 32.3% by weight of mitomycin C. The ultraviolet absorption spectrum of this product was identical with that of Example 1.

EXAMPLE 5

In the same manner as in Example 1, a solution of 545 mg of DIVEMA (average molecular weight 5,000) in 3 ml of N-methyl pyrrolidone was added to a solution of 1.0 g of 6-aminohexanoic acid in 15 ml of distilled water, with the latter solution kept stirred. During this addition, the pH of the solution was adjusted to 9.0 with an aqueous 2M sodium hydroxide solution. The resultant reaction solution was stirred at pH 9.0 for two hours. The reaction solution was diluted with 500 ml of distilled water to 500 ml, adjusted to pH 4.0 with 6M hydrochloric acid, and then subjected to ultrafiltration with a PM10 membrane (fractionation molecular weight 10,000) produced by Millipore Corp. against distilled water and freeze dried to afford 709 mg of a freeze dried product which was found to be DIVEMA having 6-aminohexanoic acid as a spacer. By causing 36 mg of the DIVEMA-6-aminohexanoic acid to react with 50 mg of mitomycin C in the same manner as in Example 1 and treating the resultant reaction product in the same manner as in Example 1, there was obtained 71 mg of a purple cotton-like solid. From the absorption of the ultraviolet spectrum at 364 nm, this product was found to contain 38.7% by weight of mitomycin C. The ultraviolet absorption spectrum of this product was identical with that of Example 1.

EXAMPLE 6

In the same manner as in Example 1, a solution of 545 mg of DIVEMA (average molecular weight 120,000) in 5 ml of N-methylpyrrolidone was added to a solution of 1.0 g of 6-aminohexanoic acid in 15 ml of distilled water, with the latter solution kept magnetically stirred. During this addition, the produced mixed solution was adjusted to pH 9.0 with an aqueous 2M sodium hydroxide solution. The resultant reaction solution was stirred at pH 9.0 for two hours. The reaction solution was diluted with 500 ml of distilled water, adjusted to pH 4.0 with 6M hydrochloric acid, and subjected to ultrafiltration with a PTHK membrane (fractional molecular weight 100,000) produced by Millipore Corp. against distilled water. The residue was freeze dried to obtain 719 mg of a freeze dried product which was found to be DIVEMA having 6-aminohexanoic acid as a spacer. By causing 36 mg of the DIVEMA-6-aminohexanoic acid to react with 50 mg of mitomycin C in the same manner as in Example 1 and treating the resultant reaction product in the same manner as in Example 1, there was obtained 72 mg of a purple cotton-like solid. From the absorption of the ultraviolet spectrum at 364 nm, this product was found to contain 39.2% by weight of mitomycin C. The ultraviolet spectrum of this product was identical with that of Example 1.

REFERENTIAL EXAMPLE 1

The macromolecular mitomycin C derivative was placed in human plasma and tested for speed of release of mitomycin C therefrom.

Figure 2:
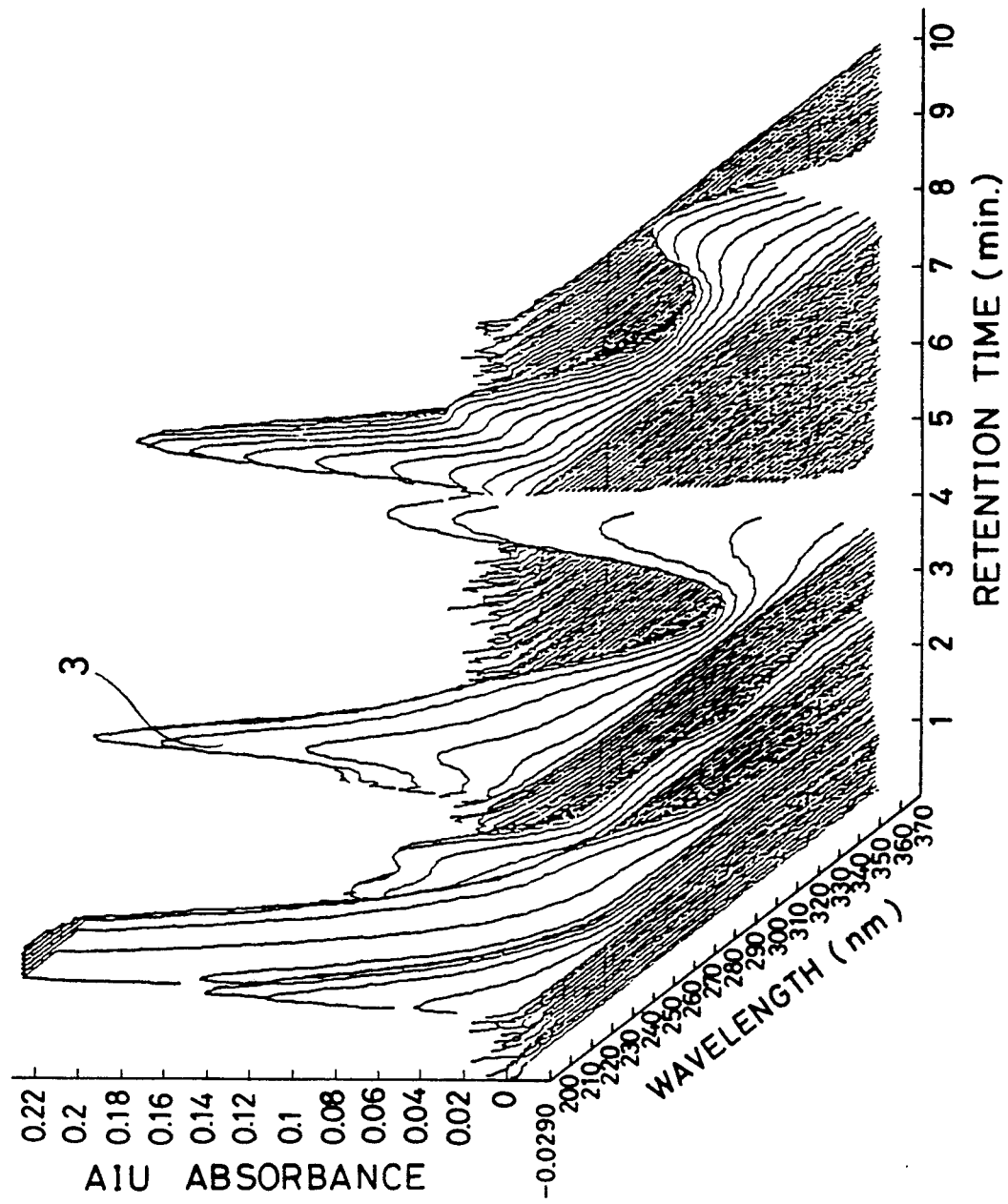
FIG. 2 is a three-dimensional spectrum of high-speed liquid chromatography evincing the release of mitomycin C from the macromolecular mitomycin C derivative of Example 1 in human plasma.
Figure 3:
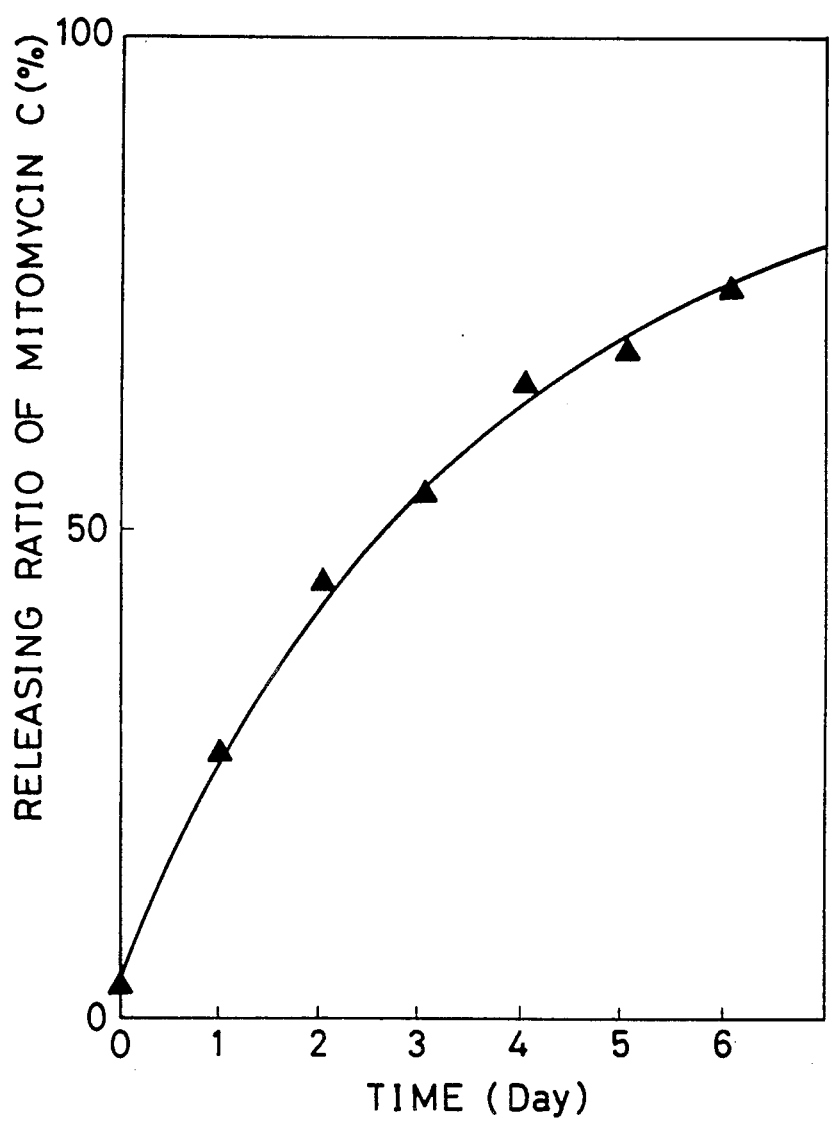
FIG. 3 is a graph showing the relation between the ratio of mitomycin C released from the macromolecular mitomycin C derivative of Example 1 in human plasma and the number of days elapsed in the test.

To be specific, 1.2 ml of human plasma having dissolved therein 6.6 mg of the macromolecular mitomycin C derivative of this invention obtained in Example 1 was left standing at 37° C At prescribed intervals, samples 50 μ in volume were taken from the plasma mixture, shaken with added methanol, and centrifuged to separate plasma protein. The released mitomycin C was separated by highspeed liquid chromatography using a reversed-phase column. The three-dimensional spectrum of the sample obtained after three days' standing is shown in FIG. 2. The peak 3 shown at the retention time of 4.1 minutes in FIG. 2 was found to be identical with mitomycin C from the ultraviolet absorption from 200 to 370 nm. FIG. 3 shows the relation between the time of standing and the ratio of release of mitomycin C. The determination of the amount of release was carried out by using cumarin 120 as an internal standard. It is clearly noted from FIG. 3 that 50% of the mitomycin C was released within 2.7 days.

REFERENTIAL EXAMPLE 2

The macromolecular mitomycin C derivative was tested for antitumor activity against mouse B16 melanotic melanoma.

In 6-week old female BD2F$_1$ mice, $1 \times 10^6$ B16 tumor cells were subcutaneously inoculated. After 12 days following the tumor inoculation, when the volume of tumor reached a level in the range of from 300 to 400 mm$^3$, the mice treated three times by intravenous injection of the macromolecular mitomycin C derivative. The mice were kept under SPF conditions. The control and treatment group consisted of 8 females of the same age. The antitumor effect of the drug was determined by measuring the major diameter and the minor diameter of the tumor with calipers, approximating the area of the tumor to an ellipse, calculating the volume of the tumor in accordance with the following formula, and comparing the volume with that found for a control group.

$$\text{Volume of tumor}(V\ mm^3) + \tfrac{1}{2}a \times b^2$$

wherein stands for the major diameter of tumor (mm) and b for the minor diameter of tumor (mm).

Table 1 shows the results found on the 22nd day after the tumor inoculation, when the mice in the control group began to die.

As this experimental method deals with the advanced stage of subcutaneously inoculated tumor by intravenous drug treatment, the result can be considered to simulate the clinical treatment. It is clearly noted from Table 1 that the macromolecular mitomycin C derivative of this invention inhibit 87.7% of the growth of tumor, a better result than 66.7% obtained by the therapy using mitomycin C at the maximum tolerated dose. These results were proved to be statistically significant by Mann-Whitney's U test (<0.05).

TABLE 1

| Drug | Dose (equivalent to MMC) | Volume of tumor (mm$^3$) | Ratio of Inhibition (%) |
|---|---|---|---|
| Macromolecular mitomycin C of this invention (39.6% content) | 3 × 12 mg/kg | 642 ± 204 | 87.7 |
| Mitomycin C | 3 × 2 mg/kg | 1597 ± 560 | 66.7 |
| DIVEMA | 3 × 7 mg/kg | 4208 ± 1803 | 12.3 |
| Control group | | 4798 ± 1602 | 0.0 |

What is claimed is:

1. A macromolecular mitomycin derivative having first repeating units represented by the formula:

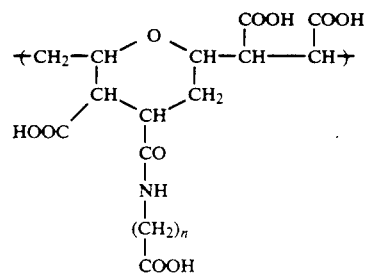

wherein n stands for an integer in the range of from 1 to 11 and second repeating units represented by the formula:

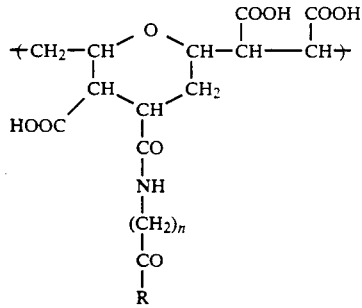

wherein R stands for a mitomycin C residue represented by the formula,

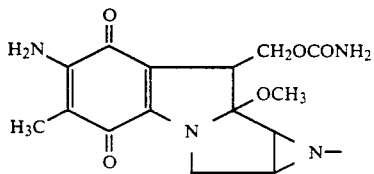

and n for an integer in the range of from 1 to 11, the total number of said first and second repeating units being not less than 10 and not more than 500, and the molar ratio of the first repeating units to the second repeating units being in the range of from 0:100 to 90:10.

2. A salt of the macromolecular mitomycin derivative set forth in claim 1.

3. A method for the production of the macromolecular mitomycin derivative set forth in claim 1, which comprises causing a divinyl ether-maleic anhydride copolymer represented by the formula:

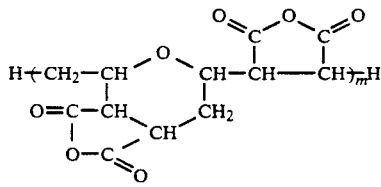

wherein m stands for an integer of not less than 10 and not more than 500 to react with an aminocarboxylic acid represented by the formula:

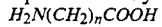

wherein n stands for an integer of not less than 1 and not more than 11 in the presence of an organic solvent and subsequently causing mitomycin C to react on the resultant reaction product.

4. A method according to claim 3, which further comprises a step of converting the final reaction product into a pharmacologically acceptable salt.

* * * * *